United States Patent (10) Patent No.: US 12,229,973 B2
Jaisson (45) Date of Patent: Feb. 18, 2025

(54) METHOD FOR REGISTERING VIRTUAL MODELS OF THE DENTAL ARCHES OF AN INDIVIDUAL WITH A DIGITAL MODEL OF THE FACE OF SAID INDIVIDUAL

(71) Applicant: MODJAW, Villeurbanne (FR)

(72) Inventor: Maxime Jaisson, Les Marches (FR)

(73) Assignee: MODJAW, Villeurbanne (FR)

( * ) Notice: Subject to any disclaimer, the term of this patent is extended or adjusted under 35 U.S.C. 154(b) by 557 days.

(21) Appl. No.: 17/437,594

(22) PCT Filed: Mar. 12, 2020

(86) PCT No.: PCT/FR2020/050526
§ 371 (c)(1),
(2) Date: Sep. 9, 2021

(87) PCT Pub. No.: WO2020/183115
PCT Pub. Date: Sep. 17, 2020

(65) Prior Publication Data
US 2022/0156953 A1 May 19, 2022

(30) Foreign Application Priority Data
Mar. 12, 2019 (FR) ...................................... 1902541

(51) Int. Cl.
*G06T 7/33* (2017.01)
*A61C 9/00* (2006.01)

(52) U.S. Cl.
CPC .............. *G06T 7/33* (2017.01); *A61C 9/0053* (2013.01); *G06T 2207/10028* (2013.01); *G06T 2207/30036* (2013.01); *G06T 2207/30204* (2013.01)

(58) Field of Classification Search
CPC ........... G06K 9/00912; G06K 9/00288; G06K 7/10297; G06K 7/10366; G06K 9/00255; G06K 9/00899
See application file for complete search history.

(56) References Cited

U.S. PATENT DOCUMENTS

2005/0163342 A1 7/2005 Persky
2007/0190481 A1* 8/2007 Schmitt ................ A61C 9/0046
433/68

(Continued)

FOREIGN PATENT DOCUMENTS

DE 10021934 A1 1/2001
DE 10216613 A1 10/2002

(Continued)

OTHER PUBLICATIONS

French Search Report in related FR application No. 869184, mailed Oct. 31, 2019.

(Continued)

*Primary Examiner* — Dhaval V Patel
(74) *Attorney, Agent, or Firm* — Thomas | Horstemeyer, LLP

(57) ABSTRACT

The invention relates to a method for registering non-radiographic virtual models of a mandibular arch and a maxillary arch of an individual with a non-radiographic digital model of the face of said individual, comprising:
fastening a mandibular marker rigidly on the mandibular arch of the individual, said mandibular marker defining a first frame of reference,
providing a non-radiographic virtual model of the mandibular arch and a non-radiographic virtual model of the maxillary arch,
digitising at least one portion of the surface of the teeth or a prosthetic device integral with said arch and at least one rigid portion of said marker by means of an intra or extra-oral camera, so as to produce a digital recording of said portions of the mandibular arch and the marker in a same second frame of reference,
from said recording and the virtual models of the mandibular arch and the mandibular marker, matching the digital model of the mandibular marker with the marker, and the virtual model of the mandibular arch with said arch, and localizing the virtual model of the mandibular arch in the first frame of reference,
acquiring a non-radiographic digital model of the face of the patient, and (Continued)

localizing the digital model of the face in the first frame of reference, so as to register the virtual models of the maxillary and mandibular arches with said digital model of the face.

6 Claims, 6 Drawing Sheets

(56) References Cited

U.S. PATENT DOCUMENTS

| | | | |
|---|---|---|---|
| 2008/0002869 A1* | 1/2008 | Scharlack | G06V 20/653 382/128 |
| 2013/0310963 A1 | 11/2013 | Davison | |
| 2018/0028292 A1* | 2/2018 | Pesach | A61C 9/004 |
| 2019/0083219 A1* | 3/2019 | Sharer | A61C 9/004 |
| 2020/0268495 A1* | 8/2020 | Ryakhovsky | A61C 11/00 |

FOREIGN PATENT DOCUMENTS

| | | |
|---|---|---|
| DE | 102013102421 A1 | 9/2014 |
| DE | 10111643 A1 | 2/2016 |
| DE | 102015211166 A1 | 12/2016 |
| DE | 10131134 A1 | 9/2018 |
| JP | 2009172411 A | 8/2009 |
| JP | 2015523871 A | 8/2015 |
| WO | 2013030511 A2 | 3/2013 |
| WO | 2016062962 A1 | 4/2016 |

OTHER PUBLICATIONS

PCT International Search Report in related PCT Application No. PCT/FR2020/050526, mailed Aug. 14, 2020.

* cited by examiner

METHOD FOR REGISTERING VIRTUAL MODELS OF THE DENTAL ARCHES OF AN INDIVIDUAL WITH A DIGITAL MODEL OF THE FACE OF SAID INDIVIDUAL

CROSS REFERENCE TO RELATED APPLICATIONS

This application is the 35 U.S.C. § 371 national stage application of PCT Application No. PCT/FR2020/050526, filed Mar. 12, 2020, which application claims the benefit of French Application No. FR 1902541, filed Mar. 12, 2019, both of which are hereby incorporated by reference herein in their entireties.

FIELD OF THE INVENTION

The present invention relates to a method for registering virtual models of the dental arches of an individual with a digital model of the face of said individual. An application of this method is taking into account aesthetic considerations during the planning of a treatment implementing an acquisition of the mandibular kinematics of the individual and the application of said kinematics to virtual models of the dental arches.

PRIOR ART

In orthodontics or in dental surgery, it is useful to animate three-dimensional (3D) virtual models of the dental arches (maxillary and mandibular) of a patient with the mandibular kinematics of said patient, in order to plan a treatment and/or to determine the effects of said treatment.

The recording of mandibular kinematics necessitates equipping the face of the patient with markers comprising objects detectable by a camera or inertial type position sensors, magnetic or other, and asking the patient to make mandibular movements. In the course of these movements, the objects are pinpointed in real time by a camera, or the position data of the sensors are recorded in real time.

Virtual 3D models of the mandibular and maxillary arches are generally obtained using an intra-oral optical scanner or by 3D digitisation of impressions of the arches or physical models of said arches. These virtual models are thus defined in a coordinate system which is associated with the digitisation device.

The markers or sensors equipping the face define a coordinate system of the patient different from the coordinate system of the virtual 3D models of the dental arches.

To animate the virtual models of the dental arches, it is necessary to transfer the movement information recorded on the patient to the virtual 3D models of the dental arches. This necessitates knowing the rigid geometric transformation (translations and rotations) making it possible to go from one coordinate system to the other.

The document WO 2013/030511 describes a method for designing a dental apparatus for an individual wherein the mandibular kinematics recorded on said individual are used to animate virtual models of the dental arches of the individual.

In a first embodiment, it is proposed to register the virtual models of the dental arches with a tomodensitometric image. However, although such an image makes it possible to visualise the position of the dental arches within the facial bones of the patient, it necessitates an irradiation of the patient by X-rays, of which it is wished to do without.

In a second embodiment, it is proposed to match the virtual models of the dental arches and a mandibular marker, by pointing in the mouth of the patient at least four determined points of the dental arches by means of a stylet. The stylet comprises objects locatable by the camera which pinpoints the mandibular marker and which are laid out according to a known geometry. It is thus possible to localize the virtual model of the mandibular arch with respect to the coordinate system of the patient attached to said arch.

An alternative to this pointing technique is described in the document WO 2016/062962, which implements a facial recognition technique. From a stereoscopic image of the face of the patient on which appear at least three teeth of the maxillary arch of the patient, said teeth are detected by a facial recognition method, and said teeth are matched on the three-dimensional surface model of the patient and on the model of the maxillary arch. However, depending on the algorithms used, this facial recognition technique may again be subject to imprecisions.

The animation of the virtual models of the dental arches based on the mandibular kinematics of the patient makes it possible to take into account occlusion aspects in the planning of a treatment.

For certain clinical applications, notably with a view to controlling the aesthetic implications of a treatment, it may be advantageous to visualise the effect of the treatment on a three-dimensional model of the face of the patient. Such a model (face scan) is typically obtained by digitising the face of the patient in three dimensions. In this case, the problem is posed of the registration of the virtual models of the dental arches with the three-dimensional model of the face of the patient.

DESCRIPTION OF THE INVENTION

An aim of the invention is thus to conceive a robust, reliable and simple to implement method for registering virtual models of the dental arches of an individual with a three-dimensional model of the face of said individual. Given the risks linked to the exposure of an individual to X-rays, the entire method must be able to be implemented with techniques not implementing X-rays (called "non-radiographic" in the remainder of the text).

To this end, the invention proposes a method for registering non-radiographic virtual models of a mandibular arch and a maxillary arch of an individual with a non-radiographic digital model of the face of said individual, characterised in that it comprises:

fastening a mandibular marker rigidly on the mandibular arch of the individual, said mandibular marker defining a first frame of reference, providing a non-radiographic virtual model of the mandibular arch and a non-radiographic virtual model of the maxillary arch, digitising at least one portion of the surface of the teeth or a prosthetic device integral with said arch and at least one rigid portion of said marker by means of an intra or extra-oral camera, so as to produce a digital recording of said portions of the mandibular arch and the marker in a same second frame of reference, from said recording and virtual models of the mandibular arch and the mandibular marker, matching the digital model of the mandibular marker with the marker, and the virtual model of the mandibular arch with said arch, and localizing the virtual model of the mandibular arch in the first frame of reference, acquiring a non-radiographic digital model of the face of the patient, and localizing the digital model of the face in the first frame of reference, so as to register the virtual models of the maxillary and mandibular arches with said digital model of the face.

"Providing" is taken to mean in the present text obtaining pre-existing virtual models or instead creating said virtual models.

Preferably, the method further comprises matching the virtual model of the maxillary arch with the virtual model of the mandibular arch in a determined occlusion position of said arches, for example a maximum intercuspal occlusion.

In certain embodiments, the method further comprises displaying the virtual models of the maxillary and mandibular arches superimposed on the digital model of the face of the patient.

In certain embodiments, the acquisition of the digital model of the face of the patient is carried out on the patient wearing a forehead marker rigidly integral with the forehead, a virtual model of said forehead marker being provided, and the registration of the virtual models of the maxillary and mandibular arches with the digital model of the face comprises matching the virtual model of the forehead marker with the forehead marker visible on said virtual model of the face.

In certain embodiments, the digital model of the face of the patient is textured, such that points traced on the face of the patient and/or anatomical characteristics are visible on said textured digital model, and the registration of the virtual models of the maxillary and mandibular arches with the digital model of the face comprises pointing points by a stylet tracked by a same localizing device as a marker equipping the face of the patient, and matching said points and/or anatomical characteristics.

In certain embodiments, the acquisition of the digital model of the face of the patient is carried out on the patient wearing a forehead marker rigidly integral with the forehead, a virtual model of said forehead marker being provided, points traced beforehand on the face of the patient and/or anatomical characteristics being visible on the digital model of the face of the patient, and the registration of the virtual models of the maxillary and mandibular arches with the digital model of the face comprises pointing said points by a stylet tracked by a same localizing device as the forehead marker, and matching said pointed points and the points visible on the digital model of the face of the patient.

In certain embodiments, the digital model of the face of the patient is non-textured, and, during the acquisition of the digital model of the face, recognisable geometric shapes are fastened on the face of the patient, and the registration of the virtual models of the maxillary and mandibular arches with the digital model of the face comprises pointing said geometric shapes by a stylet tracked by a same localizing device as a marker equipping the face of the patient, and matching said pointed geometric shapes and the geometric shapes detectable on the digital model of the face of the patient.

BRIEF DESCRIPTION OF THE FIGURES

Other characteristics and advantages of the invention will become clear from the detailed description that follows, with reference to the appended drawings in which.

DETAILED DESCRIPTION OF EMBODIMENTS OF THE INVENTION

Figure 1:
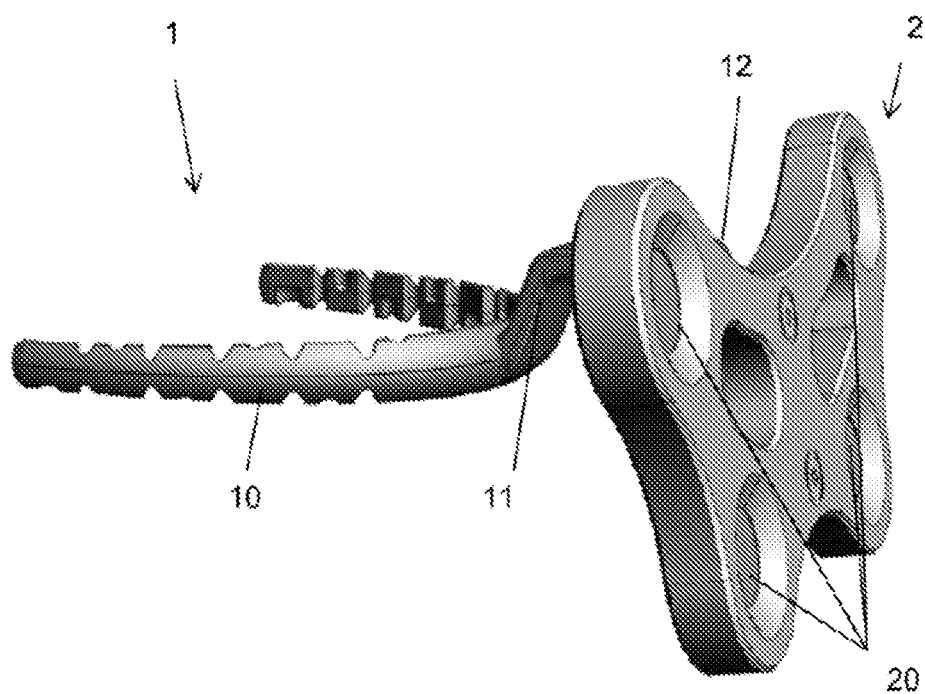
FIG. 1 is a perspective view of a mandibular fastening device equipped with a localization marker.

The invention proposes using, on the one hand, an intra-oral scanner—or an extra-oral camera in an alternative embodiment—to scan simultaneously the surface of the teeth of a dental arch and at least one portion of a marker fastened on said arch or a portion of the device for fastening the marker on the arch if appropriate and, on the other hand, a device for digitising the face of the individual. The result of these operations is a digital recording of at least one portion of the arch and at least one portion of the marker, in a same frame of reference which is that of the intra-oral scanner, as well as a digital recording of the surface of the face. As described in detail below, these recordings make it possible to register the virtual models of the dental arches with the digital model of the face of the patient by means of the frame of reference associated with the marker.

This registration method is implemented by a computer which comprises a processor configured to implement algorithms for image analysis and computation of rigid transformations between models defined in different coordinate systems. The computer comprises a screen coupled to the processor and configured to display the virtual models of the dental arches as well as the other images implemented in the method described below.

Virtual Models of the Dental Arches

The virtual models of the dental arches may be obtained by any appropriate non-radiographic technique. Among the most widely used techniques may be cited, in a non-limiting manner, the digitisation of impressions or physical models (for example made of plaster or resin) of the arches of the patient, by means of a laboratory scanner, or instead direct digitisation in the mouth of the patient, by means of an intra-oral scanner.

When an arch is totally or partially toothless, it is known to fasten thereto a prosthetic device, also called occlusal model, which comprises a base covering the prosthetic bearing surface and a bead replacing the teeth and the alveolar bone. A virtual model of said device is obtained from the plan thereof produced by computer aided design (CAD). In this case, the virtual model of the dental arch is that of the arch provided with said device.

Whatever the technique used, the digitisation is carried out for each arch taken separately, and for the two dental arches in occlusion situation. In this occlusion situation, the two arches are scanned in the same frame of reference, which makes it possible to establish a relationship between the virtual models of the two arches.

The creation of these virtual models may be carried out before the implementation of the registration method according to the invention, or concomitantly therewith.

Markers

To track the movements of the mandibular arch with respect to the maxillary arch, the patient is equipped at least with a mandibular marker, which defines a coordinate system attached to the face of the patient.

According to an embodiment, the patient is also equipped with a maxillary marker. In an alternative manner to the use of a maxillary marker, the face of the patient itself may be used as "marker"; thanks to a facial recognition algorithm, it is possible to track in real time by a scanner several elements characteristic of the upper portion of the face, which will be associated with the model of the maxillary arch. The upper portion of the face is in fact considered as sufficiently non-deformable to not require a marker as such.

According to an embodiment, each marker comprises several reflective chips laid out according to a determined geometry. Each marker is tracked by a scanner and the pinpointing of the position of the chips makes it possible to localize the marker in space.

According to other embodiments, the markers may comprise chips having a two-colour pattern of known geometry, diodes, inertial sensors, etc. which also make it possible to localize each marker in space by means of a corresponding localizing device. Those skilled in the art are able to choose the appropriate localizing device and the associated marker(s) among the technologies present on the market.

Mandibular Marker

The mandibular marker is rigidly attached to the mandible of the patient, that is to say that it is fastened so as not to move with respect to the mandible in the course of mandibular movements made by the patient. The mandibular marker may be attached to the arch directly (the marker then integrating a means for fastening to the arch) or by means of a fastening device with which it is integral.

The document WO 2018/158551 describes a mandibular marker that may be used in the present invention.

In the example illustrated in FIG. 1, the marker 2 comprises four reflective chips 20, the size and the relative position of which are known, detectable by an infrared camera. The shape of the chips is not limiting. Thus, said chips could be replaced by reflective elements having any other appropriate shape, for example beads. Alternatively, the reflective chips could be replaced by a target formed of a two-colour pattern of known geometry. According to other embodiments, the reflective chips could be replaced by diodes, electromagnetic coils, or any other appropriate localizing means, such as inertial sensors (IMUs, inertial measurement units), accelerometers, gyroscopes, etc.

The marker 2 is attached to the mandibular arch by means of a fastening device 1 on which it is removably mounted. The device 1 comprises:
- an intra-oral portion 10 intended to be maintained against the outer face of the teeth of the lower jaw (not represented),
- an extra-oral portion 12 (more clearly visible in FIG. 2) comprising an element for fastening the marker 2,
- a linking portion 11 making it possible to connect the intra-oral portion 10 to the extra-oral portion 12.

In a particularly advantageous manner, the assembly of the three portions 10, 11, 12 is formed of one piece, by moulding of a biocompatible thermoplastic material.

The intra-oral portion 10 has a general U shape.

The material and the thickness of the intra-oral portion are chosen to have a certain flexibility in a direction of moving apart or bringing closer the legs of the U in their plane. Thus, the two legs 100 may be moved apart with respect to their initial position to be inserted into the mouth of the individual without rubbing against the teeth or the gums, then released once they have been correctly positioned.

According to an optional but advantageous embodiment, the end of the legs of the U is made breakable by the presence of one or more notches 101 which define one or more detachable segments 102. Thus, one or more of said detachable segments may be removed until a length of the legs 100 suited to the length of the jaw of the individual is obtained.

Advantageously, the mechanical strength of the intra-oral portion 10 on the jaw of the patient is ensured at least in part by a biocompatible adhesive (not represented) deposited between the surface of the teeth and the lower face of the intra-oral portion. Such a biocompatible adhesive is frequently used in the dentistry field.

Furthermore, the lower face 103 of the intra-oral portion, that is to say the face intended to come into contact with the teeth, may have a certain roughness. For example, a part derived from 3D printing (SLS (selective laser sintering) technique) has an appropriate roughness. In the case of a part derived from moulding, the injection mould may undergo a treatment, for example a sanding or chemical etching, conferring thereon a non-smooth surface. This roughness makes it possible to improve the mechanical strength of the adhesive vis-à-vis the inner face 103.

Furthermore, the inner face 103 of the intra-oral portion may be provided with notches 104. Said notches are laid out in such a way as to be facing portions in relief on the outer surface of the teeth when the device is in place in the mouth of the individual. The notches 104 thus fulfil a function of blocking the intra-oral portion, notably in the antero-posterior direction, which stabilises the device in the mouth.

In a particularly advantageous manner, the height h of the intra-oral portion is chosen sufficiently small (typically less than the average height of the teeth) in order not to extend beyond the plane formed by the upper surface of the teeth of the lower jaw when the device is in place in the mouth of the individual. For example, the height h is of the order of 5 mm.

Thus, the intra-oral portion does not interfere with the mandibular kinetics (clenching of the teeth, mastication movements and others).

The extra-oral portion 12 has for its part a fastening element 120 for a marker.

Figure 2:
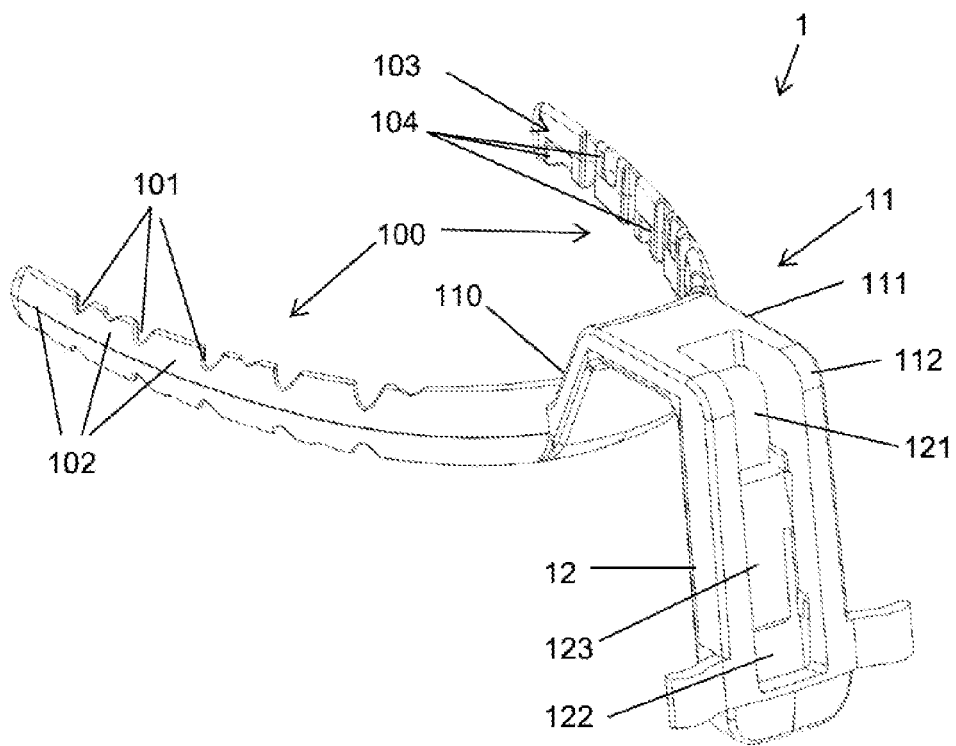
FIG. 2 is a perspective view of the mandibular fastening device of FIG. 1 in the absence of the localization marker.

In the example illustrated in FIGS. 1 and 2, the marker 2 is fastened by snap locking on the extra-oral portion 12. To this end, the mandibular marker 2 comprises, on its inner face (i.e. opposite to the reflective chips), two lugs laid out one above the other (considering the position of the marker when it is in place on the individual). The fastening element 120 comprises two housings 121, 122 separated by an elastic tongue 123. To put in place the marker 2 on the fastening device 1, the upper lug is firstly engaged in the housing, then the lower lug is engaged in the housing 122, this engagement causing a slight deformation of the tongue 123 backwards (that is to say on the side opposite to the reflective chips). The marker is thus maintained on the extra-oral portion 12 by engagement of the lugs in the housings 121, 122 and by a pressure force exerted by the deformed tongue 123.

The assembly of the marker 2 on the fastening device is advantageously carried out once the fastening device has been put in place in the mouth of the patient and fastened using the aforementioned biocompatible adhesive. Thus, the marker does not impede this putting in place operation. The force necessary to put the marker in place on the extra-oral portion is very small, such that it does not affect the mechanical strength of the fastening device vis-à-vis the mandibular arch.

The extra-oral portion is designed to be sufficiently rigid to support the weight of said marker without being deformed.

According to a less preferred embodiment, the marker could form an integral part of the extra-oral portion.

When the device 1 is in place in the mouth of the individual, the extra-oral portion 12 is advantageously situated below the plane of the lips of the individual (the marker 20 being able for its part to extend beyond this plane).

For reasons of stability of the device, said device is substantially symmetrical with respect to the antero-posterior plane of the individual.

The linking portion 11 between the intra-oral 10 and extra-oral 12 portions is like a bridge fitting extending from the central region of the intra-oral portion 10. This bridge fitting has a first section 110 extending towards the upper jaw, a second section 111 extending through the lips and a third section 112 for connecting to the extra-oral portion 12. The shape and the dimensions of the linking portion are chosen so that, when the device is in place in the mouth of the individual, the second section 111 extends to the level of the plane of the lips, without exerting pressure on the lips. Thus, the device 1 remains immobile even in the event of swallowing.

Furthermore, the linking portion 11 is designed to be sufficiently rigid so as not to deform when the marker 20 is fastened to the extra-oral portion 12.

Maxillary Marker

The maxillary marker is attached to the maxillary of the patient or to another element of the face rigidly integral with the maxillary, for example the forehead. In this case, the term forehead marker is used.

The maxillary or forehead marker is preferably based on the same technology as the mandibular marker. For example, the maxillary marker comprises several reflective chips laid out according to a determined pattern.

According to an embodiment, the forehead marker is in the form of a frame intended to surround the forehead of the patient and suitable for bearing on the ears and on the nasal bridge, which stabilises it.

Virtual models of the mandibular and maxillary markers (and, if appropriate, their fastening device if said device is in the form of a separate component) are generally obtained from the plans thereof produced by computer aided design (CAD).

As indicated above, it is possible to do without the use of a maxillary or forehead marker using a facial recognition algorithm to track the movements of the upper portion of the face of the patient.

Registration of the Virtual Models of the Dental Arches with a Frame of Reference of the Patient The registration involves the use of an intra-oral impression camera (also known as an intra-oral scanner) or any other non-radiographic intra-oral system suitable for digitising the surface of one or both arches (and/or, if appropriate, a prosthetic device rigidly linked to an arch) so as to form point clouds or grids.

However, compared to the normal use of such an intra-oral device, where the practitioner only scans the surface of the teeth with a view to creating a virtual model of the corresponding arch, the invention also involves scanning at least one portion of the mandibular marker rigidly linked to the mandibular arch.

Figure 3:
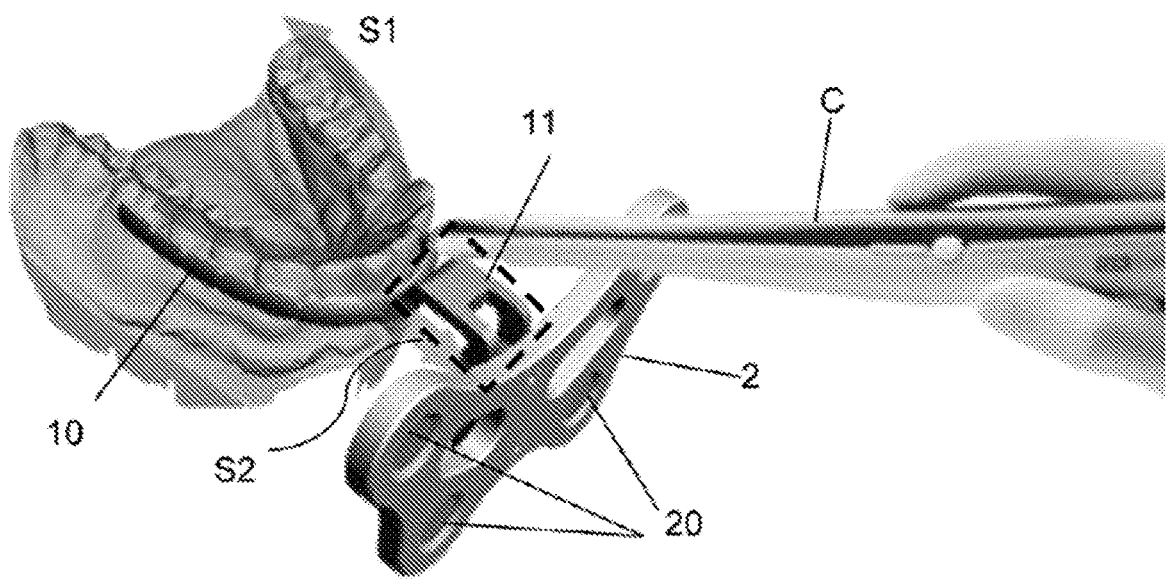
FIG. 3 is a schematic diagram of the digitisation of the mandibular arch and a portion of the mandibular marker by means of an intra-oral scanner.

FIG. 3 is a schematic diagram of this operation, with a mandibular marker 2 and a mandibular fastening device 1 of the marker such as described with reference to FIGS. 1 and 2. The intra-oral impression camera C is introduced into the mouth of the patient, the mandibular arch being equipped beforehand with the mandibular marker 2.

The practitioner scans with the camera C the surface of the teeth of the mandibular arch and, if appropriate, the aforementioned prosthetic device, for example according to the movement shown schematically by the arrow S1.

The practitioner also carries out a scanning with the camera C of the linking portion 11, shown schematically by the arrow S2. The scanned zone is surrounded by dotted lines.

A digital recording is thus obtained in the form of a point cloud or a grid comprising not only at least one portion of the surface of the teeth and/or a prosthetic device integral with the arch but also the linking portion 11, in a same frame of reference.

Knowing the geometry of this linking portion 11, notably by the CAD model of the fastening device, the marker may be matched with its virtual model by correlation of the shape of the linking portion 11 on the intra-oral scan and on the virtual model.

Similarly, the dental arch may be matched with its virtual model by correlation of the surface of the teeth on the intra-oral scan and on the virtual model. In the case where a prosthetic device is integral with the arch, knowledge of the virtual model of said device makes it possible to determine the emplacement of the toothless gum.

The mandibular arch and the mandibular marker (or at least the linking portion 11) having been scanned in the same frame of reference by the intra-oral scanner, the virtual model of the mandibular arch may be localized in the coordinate system of the mandibular marker, which defines the coordinate system of the patient attached to the mandibular arch.

The complete digitisation of the marker is not necessary from the moment that a sufficient non-deformable portion is digitised and may be correlated with the virtual model of said portion. The correlation is all the more robust when the digitised portion has specific geometric characteristics. In this respect, it is indifferent whether the marker is made of one piece or not with the fastening device, from the moment that the portion scanned by the intra-oral scanner is sufficiently rigid. By extension, in the present text, the expression "digitisation of at least one rigid portion of the marker" covers the digitisation of a rigid portion of the fastening device on which the marker is attached rigidly and in a reproducible manner.

In the case where the mandibular marker is formed in one piece with the mandibular fastening device, it comprises an intra-oral portion that is deformable to adapt to the morphology of the patient and a non-deformable portion provided with reflective chips or other detectable objects. The intra-oral scan must then concern a sufficient portion of the non-deformable portion. On the other hand, the intra-oral portion is not in principle sufficient to carry out the registration because it is too deformable.

According to a particular embodiment, the creation of the virtual model of the mandibular arch may be carried out during said intra-oral scan operation; the virtual model of the mandibular arch and the information necessary for the registration are thus obtained in a single step. However, the presence of the mandibular marker masks a portion of the surface of the teeth and is thus liable to decrease the precision of the virtual model of the mandibular arch.

Alternatively to the use of an intra-oral scanner, the digitisation of the surface of a portion of the teeth and a sufficient portion of the mandibular marker may be carried out using a non-radiographic extra-oral camera. Said extra-oral camera carries out a three-dimensional acquisition of the general shape of the mandibular marker and the visible teeth of the mandibular arch, in a same frame of reference. The virtual models, more precise, of the mandibular marker and the mandibular arch may then be matched according to the same principle as described above.

Another technique to acquire simultaneously, in a same frame of reference, the three-dimensional shape of a portion of the mandibular marker and a portion of the mandibular arch is photogrammetry. In a manner known per se, this non-radiographic technique consists in taking photographs under different angles where the teeth and the marker are visible. From this series of photographs, the geometry of the marker is recognised as well as that of the mandibular arch.

The same registration method may be applied to localize the virtual model of the maxillary arch in the coordinate system of a maxillary or forehead marker. In the case of a maxillary marker (for example of the same type as the mandibular marker with a fastening device comprising an intra-oral portion having a general U shape), the intra-oral scanner is used to digitise simultaneously at least one portion of the surface of the teeth (and/or a prosthetic device such as described previously) of the maxillary arch and a sufficient rigid portion of the mandibular marker or its fastening device). In the case of a forehead marker, the extra-oral camera is used to digitise simultaneously at least one portion of the surface of the teeth (and/or a prosthetic device such as described previously) of the maxillary arch and the forehead marker.

According to another embodiment, a marker is rigidly linked to the forehead of the patient and thus defines a coordinate system of the maxillary arch. By placing the patient in a known occlusion position of the arches (generally the maximum intercuspal occlusion (MIO), which is that used during the creation of the virtual models of the arches), the model of the maxillary arch is brought opposite the mandibular arch. In this situation, the position of the maxillary marker with respect to the mandibular marker is known thanks to a recording made by the extra-oral camera. The model of the maxillary arch may thus be associated with the maxillary marker. All of the points, axes and reference planes of the patient are then associated with the virtual models of the arches.

Digitisation of the Face of the Patient

A three-dimensional digital model of the face of the patient is typically obtained by digitisation of the face of the patient in three dimensions. According to the digitisation technique used, this model may comprise or not a texture of the face (in particular colours).

This digitisation may be carried out by means of the following techniques: stereoscopy, photogrammetry, laser scanning associated or not with a RGB (red, green, blue) colour detection sensor, structured light and/or time of flight (TOF) measurement.

During this digitisation, the patient may be equipped with a maxillary or forehead marker such as mentioned above.

Registration of the Virtual Models of the Dental Arches with the Digital Model of the Face of the Patient The registration of the virtual models of the dental arches with the digital model of the face of the patient implements the frame of reference of the patient mentioned above.

Figure 4A:
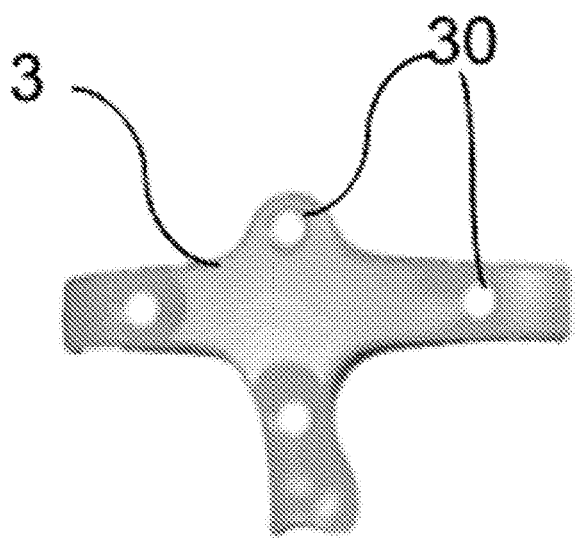
FIG. 4A is a view of a virtual model of a forehead marker and virtual models of the dental arches.
Figure 4A:
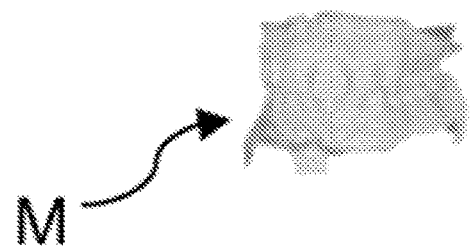
Figure 4B:
FIG. 4B is a view of a digital model of the face of an individual wearing the forehead marker of FIG. 4A.
Figure 4C:
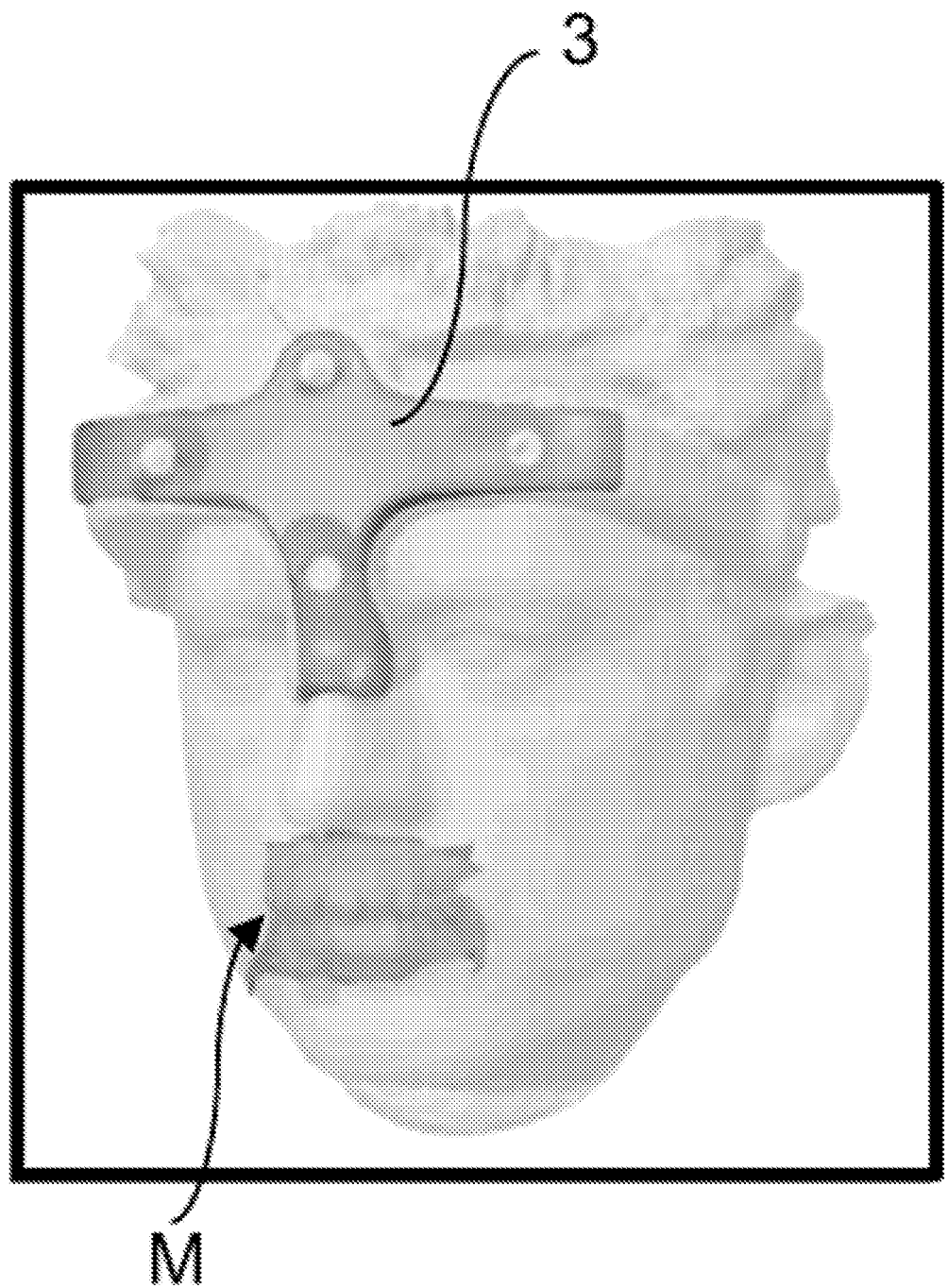
FIG. 4C is a view of the superposition of virtual models of the dental arches and the virtual model of the forehead marker of FIG. 4A on the digital model of the face of the individual.

According to an embodiment illustrated in FIGS. 4A to 4C, the marker of the maxillary arch is arranged on the forehead of the patient during the digitisation of the face of the patient. In this embodiment, this marker 3 comprises reflective chips 30 arranged according to a known geometry (cf. FIG. 4A), but, as indicated above for the mandibular marker, other localizing techniques could be used. The virtual model of the marker 3 is obtained for example by its CAD plan.

The virtual models M of the dental arches are furthermore obtained by one of the aforementioned techniques.

As illustrated in FIG. 4B, the marker 3 is locatable on the digital model of the face of the patient. It is thus possible to match this model of the face of the patient with the virtual model of the marker 3.

As illustrated in FIG. 4C, the virtual models M of the dental arches having been matched beforehand with the virtual model of the forehead marker thanks to one of the methods described previously, it is then possible to correlate said virtual models of the dental arches with the 3D model of the face of the patient, and to display said models M superimposed on the model of the face of the patient.

Optionally, a digital model of the face of the patient may be generated while the patient is not wearing the forehead marker, and is matched with the digital model of the face of the patient wearing the forehead marker by recognition of the shapes of the grids of the two models. Thereafter, the virtual models of the dental arches may be displayed on the model of the face of the patient without the forehead marker.

Thus, it is possible to visualise the dental arches whatever the position of the mouth of the patient. In particular, this matching may be carried out even if no tooth is visible on the image of the face of the patient. Furthermore, this solution makes it possible to offset the defect of resolution of certain digital models of the face, which do not make it possible to discern the shape of the teeth even when smiling, and thus enable a correlation of the virtual models of the dental arches with the digital model of the face.

According to an embodiment able to be implemented with a textured digital model of the face, in an alternative to the use of the forehead marker or in association therewith, the registration may be done using points traced on the face of the patient or placed on the face in the form of stickers, and/or anatomical characteristics of the face, such as beauty spots, scars, etc. These points or characteristics are also visible on the texture of the digital model of the face. The practitioner then uses a stylet such as described in the introductory part of the present text, and points using the stylet to the different identified points or characteristics. Each action of pointing by the stylet generates a corresponding point in space in the form of a sphere. The stylet being pinpointed by the camera at the same time as the forehead marker, the position of the spheres is determined in the coordinate system of the forehead marker.

Optionally, the registration between the model of the face and the virtual models of the dental arches may be carried out uniquely using points and anatomical characteristics of the face, without pinpointing the forehead marker on the model of the face. In this case, the patient is equipped with a mandibular marker for the operation of registration of the mandibular arch with the mandibular marker, as described previously. The pointing of the points and/or anatomical characteristics of the patient is then carried out using the stylet as explained previously. This pointing makes it possible to match the spheres generated by each action of pointing of the stylet and the coordinate systems associated with the mandibular and maxillary markers. Before or after this operation, the digitisation of the face of the patient is furthermore carried out, without any marker on the patient, so as to generate a textured digital model of the face. The points or anatomical characteristics pointed using the stylet being visible on said textured digital model, and correlated with the virtual models of the mandibular arch and the maxillary arch, it is thus possible to match the virtual models of the mandibular arch and the maxillary arch and the digital model of the face.

Figure 5A:
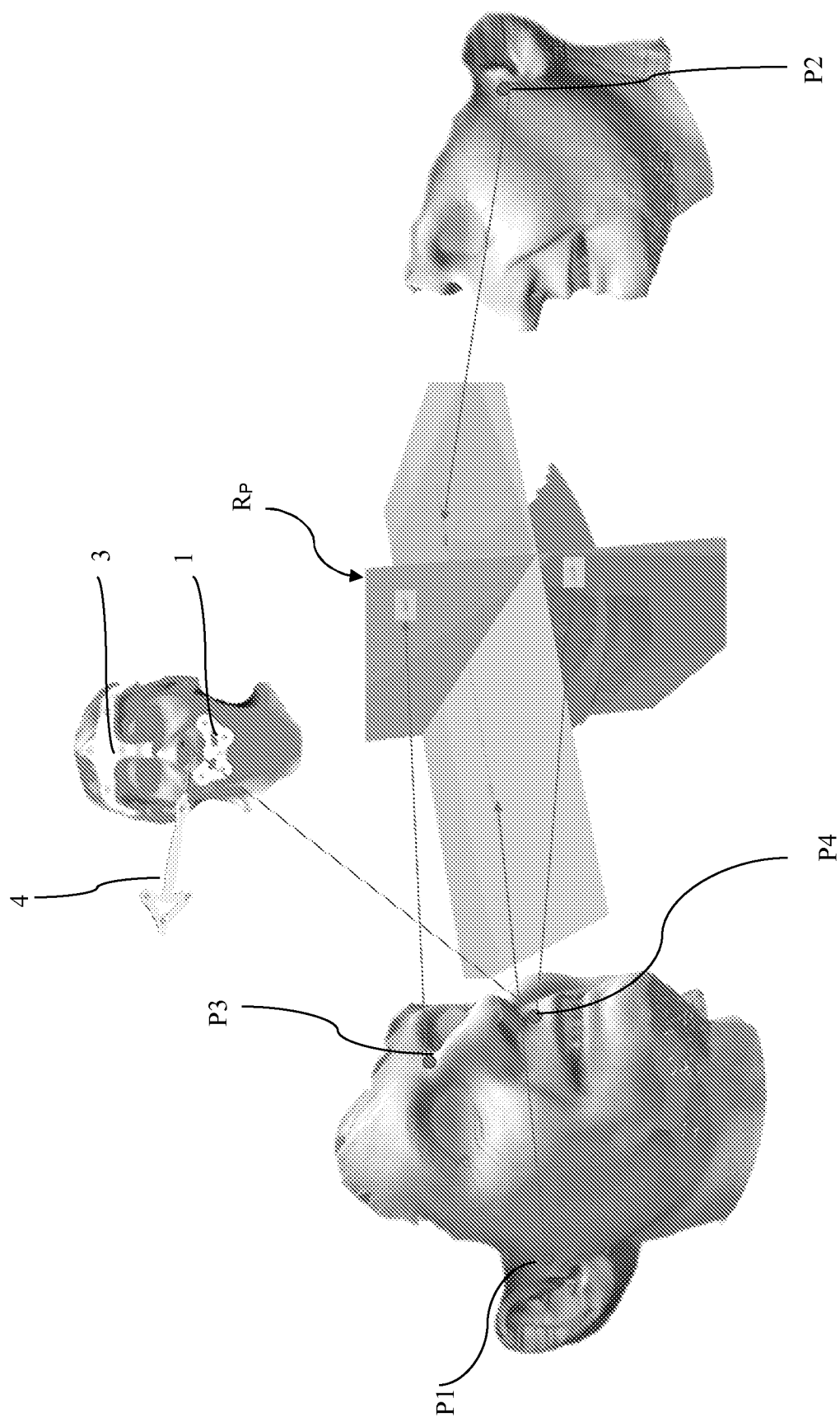
FIG. 5A is a diagram of another principle of registration of digital models of the dental arches with the digital model of the face.
Figure 5B:
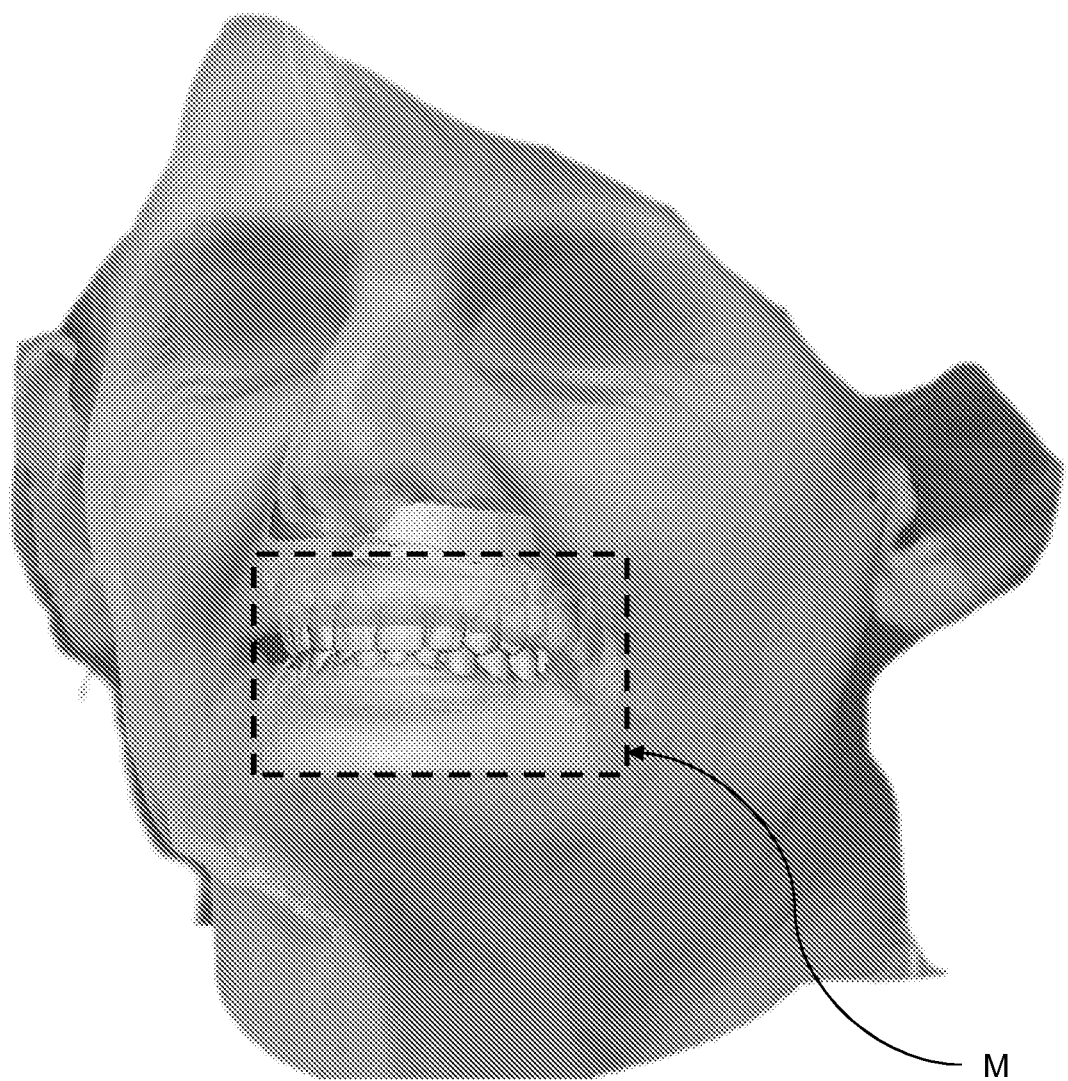
FIG. 5B is a view of the superposition of the virtual models of the dental arches on the digital model of the face of the individual at the end of the registration of FIG. 5A.

This embodiment is illustrated in FIGS. 5A and 5B.

As illustrated in the upper part of FIG. 5A, the patient is equipped with the mandibular marker and the forehead marker 3 for the acquisition of the mandibular kinematics.

The digital model of the face of the patient (the left and right sides of whom may be seen in FIG. 5A), is obtained while the patient is not wearing the mandibular marker nor the forehead marker. However, points of colour P1-P4 situated at the level of anatomical points characteristic of the face, such as respectively the two condyles, the tip of the nose and the interval between the base of the nose and the upper lip, are visible on the digital model in colour.

The matching of the models is made possible thanks to the pointing of these same points P1-P4 with the stylet 4 when the patient is equipped with the mandibular marker and the forehead marker.

These points define a frame of reference of the patient $R_P$ which is common to the virtual models of the dental arches and to the digital model of the face.

FIG. 5B illustrates the result of the registration, enabling a superposition of the virtual models of the dental arches on the digital model of the face of the patient.

In the case where the digital model of the face is not textured, it is possible to fasten onto the face of the patient, before the digitisation of the face, geometric shapes recognisable by an image processing algorithm. Advantageously, these geometric shapes comprise an emplacement suitable for the stylet, for example a hollow of dimensions suitable for receiving the tip of the stylet.

The matching of the models is then made possible thanks to the pointing of these emplacements with the stylet when the patient is equipped with the mandibular marker and the forehead marker.

The combination of the pinpointing of the forehead marker on the digital model of the face and the pointing of the points or anatomical characteristics makes it possible to increase the robustness of the method of registration between the virtual models of the arches and the digital model of the face. In particular, the face being less rigid than the dental arches, due to the mobility of the muscles or the sinking of the skin during the application of the stylet, there may be differences between the digital model of the face with and without marker.

Naturally, the representations of the markers on the appended figures are given uniquely for illustration purposes and those skilled in the art will be able to choose any other shape of marker having a rigid portion suited to the registration method described above.

The invention claimed is:

1. A method for registering non-radiographic virtual models of a mandibular arch and a maxillary arch of an individual with a non-radiographic digital model of a face of said individual, comprising:
fastening a mandibular marker rigidly on the mandibular arch of the individual, said mandibular marker defining a first frame of reference,
providing a non-radiographic virtual model of the mandibular arch and a non-radiographic virtual model of the maxillary arch,
digitising at least one portion of the surface of the teeth or a prosthetic device integral with the mandibular arch and at least one rigid portion of said marker by means of an intra or extra-oral camera, so as to produce a digitised recording of said portions of the mandibular arch and the marker in a same second frame of reference,
from said recording and the virtual models of the mandibular arch and the mandibular marker, matching the digital model of the mandibular marker with the marker, and the virtual model of the mandibular arch with the mandibular arch, and localizing the virtual model of the mandibular arch in the first frame of reference,
acquiring a non-radiographic digital model of the face of the individual, and
localizing the non-radiographic digital model of the face in the first frame of reference, so as to register the virtual models of the maxillary and mandibular arches with said digital model of the face,
wherein the digital model of the face of the individual is textured, such that points traced on the face of the individual and/or anatomical characteristics are visible on said textured digital model, and the registration of the virtual models of the maxillary and mandibular arches with the digital model of the face comprises pointing points by a stylet tracked by a same localizing device as a marker equipping the face of the individual, and matching said pointed points and/or anatomical characteristics and points visible on the digital model of the face of the individual.

2. The method of claim 1, further comprising matching the virtual model of the maxillary arch with the virtual model of the mandibular arch in a determined occlusion position of said arches.

3. The method of claim 1, further comprising displaying the virtual models of the maxillary and mandibular arches superimposed on the digital model of the face of the individual.

4. The method of claim 1, wherein the acquisition of the digital model of the face of the individual is carried out on the individual wearing a forehead marker rigidly integral with the forehead, a virtual model of said forehead marker being provided, and the registration of the virtual models of the maxillary and mandibular arches with the digital model of the face comprises matching the virtual model of the forehead marker with the forehead marker visible on said virtual model of the face.

5. A method for registering non-radiographic virtual models of a mandibular arch and a maxillary arch of an individual with a non-radiographic digital model of a face of said individual, comprising:
fastening a mandibular marker rigidly on the mandibular arch of the individual, said mandibular marker defining a first frame of reference,
providing a non-radiographic virtual model of the mandibular arch and a non-radiographic virtual model of the maxillary arch,
digitising at least one portion of the surface of the teeth or a prosthetic device integral with the mandibular arch and at least one rigid portion of said marker by means of an intra or extra-oral camera, so as to produce a digitised recording of said portions of the mandibular arch and the marker in a same second frame of reference,
from said recording and the virtual models of the mandibular arch and the mandibular marker, matching the digital model of the mandibular marker with the marker, and the virtual model of the mandibular arch with the mandibular arch, and localizing the virtual model of the mandibular arch in the first frame of reference, acquiring a non-radiographic digital model of the face of the individual, and localizing the non-radiographic digital model of the face in the first frame of reference, so as to register the virtual models of the maxillary and mandibular arches with said digital model of the face, wherein the acquisition of the digital model of the face of the individual is carried out on the individual wearing a forehead marker rigidly integral with the forehead, a virtual model of said forehead marker being provided, points traced beforehand on the face of the individual and/or anatomical characteristics being visible on the digital model of the face of the individual, and the registration of the virtual models of the maxillary and mandibular arches with the digital model of the face comprises pointing said points by a stylet tracked by a same localizing device as the forehead marker, and matching said pointed points and points visible on the digital model of the face of the individual.

6. A method for registering non-radiographic virtual models of a mandibular arch and a maxillary arch of an individual with a non-radiographic digital model of a face of said individual, comprising:

fastening a mandibular marker rigidly on the mandibular arch of the individual, said mandibular marker defining a first frame of reference, providing a non-radiographic virtual model of the mandibular arch and a non-radiographic virtual model of the maxillary arch, digitising at least one portion of the surface of the teeth or a prosthetic device integral with the mandibular arch and at least one rigid portion of said marker by means of an intra or extra-oral camera, so as to produce a digitised recording of said portions of the mandibular arch and the marker in a same second frame of reference, from said recording and the virtual models of the mandibular arch and the mandibular marker, matching the digital model of the mandibular marker with the marker, and the virtual model of the mandibular arch with the mandibular arch, and localizing the virtual model of the mandibular arch in the first frame of reference, acquiring a non-radiographic digital model of the face of the individual, and localizing the non-radiographic digital model of the face in the first frame of reference, so as to register the virtual models of the maxillary and mandibular arches with said digital model of the face, wherein the digital model of the face of the individual is non-textured, and wherein, during the acquisition of the digital model of the face, recognisable geometric shapes are fastened on the face of the individual, and the registration of the virtual models of the maxillary and mandibular arches with the digital model of the face comprises pointing said geometric shapes by a stylet tracked by a same localizing device as a marker equipping the face of the individual, and matching said pointed geometric shapes and the geometric shapes detectable on the digital model of the face of the individual.

\* \* \* \* \*